United States Patent
Siejko et al.

(10) Patent No.: US 9,272,151 B2
(45) Date of Patent: Mar. 1, 2016

(54) ADAPTIVE PHRENIC NERVE STIMULATION DETECTION

(71) Applicant: Cardiac Pacemakers, Inc., St. Paul, MN (US)

(72) Inventors: Krzysztof Z. Siejko, Maple Grove, MN (US); Sunipa Saha, Shoreview, MN (US); Aaron R. McCabe, Edina, MN (US); Holly Rockweiler, Minneapolis, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 202 days.

(21) Appl. No.: 13/939,790

(22) Filed: Jul. 11, 2013

(65) Prior Publication Data
US 2014/0018872 A1    Jan. 16, 2014

Related U.S. Application Data

(60) Provisional application No. 61/670,870, filed on Jul. 12, 2012.

(51) Int. Cl.
*A61N 1/37* (2006.01)
*A61B 5/00* (2006.01)
*A61B 5/04* (2006.01)
(Continued)

(52) U.S. Cl.
CPC .......... *A61N 1/3706* (2013.01); *A61B 5/04001* (2013.01); *A61B 5/4041* (2013.01); *A61B 5/4836* (2013.01); *A61B 5/7235* (2013.01);
(Continued)

(58) Field of Classification Search
CPC ............. A61B 5/04001; A61B 5/0488; A61B 5/4041; A61B 5/4836; A61B 5/7235; A61N 1/3686; A61N 1/3706; A61N 1/371
See application file for complete search history.

(56) References Cited

U.S. PATENT DOCUMENTS 7,142,919 B2    11/2006    Hine et al.
7,299,093 B2    11/2007    Zhu et al.
(Continued)

FOREIGN PATENT DOCUMENTS

WO    WO-2013148053 A1    10/2013

OTHER PUBLICATIONS

Dong, Yanting, et al., "Determination of Phrenic Nerve Stimulation Threshold", U.S. Appl. No. 13/781,042, filed Feb. 28, 2013.
(Continued)

*Primary Examiner* — Rex R Holmes
(74) *Attorney, Agent, or Firm* — Schwegman Lunberg & Woessner, P.A.

(57) ABSTRACT

An example of a system comprises a cardiac pulse generator configured to generate cardiac paces to pace the heart, a sensor configured to sense a physiological signal for use in detecting pace-induced phrenic nerve stimulation (PS), a storage, and a phrenic nerve stimulation detector. The storage is configured for use to store patient-specific PS features for PS beats with a desirably large signal-to-noise ratio. The phrenic nerve stimulation detector may be configured to detect PS features for the patient by analyzing a PS beat with a desirably large signal-to-noise ratio induced using a pacing pulse with a large energy output and store patient-specific PS features in the storage, and use the patient-specific PS features stored in the memory to detect PS beats when the heart is paced heart using cardiac pacing pulses with a smaller energy output.

20 Claims, 10 Drawing Sheets

(51) Int. Cl.
*A61N 1/368* (2006.01)
*A61B 5/0488* (2006.01)

(52) U.S. Cl.
CPC .............. *A61N 1/3686* (2013.01); *A61N 1/371* (2013.01); *A61B 5/0488* (2013.01)

(56) References Cited

U.S. PATENT DOCUMENTS

| | | |
|---|---|---|
| 7,354,404 B2 | 4/2008 | Kim et al. |
| 7,426,412 B1 | 9/2008 | Schecter |
| 7,477,932 B2 | 1/2009 | Lee et al. |
| 7,499,751 B2 | 3/2009 | Meyer et al. |
| 7,636,599 B1 | 12/2009 | Koh et al. |
| 7,972,276 B1 | 7/2011 | Min |
| 8,326,418 B2 | 12/2012 | Sommer et al. |
| 8,326,420 B2 | 12/2012 | Skelton et al. |
| 8,527,051 B1 | 9/2013 | Hedberg et al. |
| 8,532,774 B1 | 9/2013 | Hedberg et al. |
| 8,626,292 B2 | 1/2014 | Mccabe et al. |
| 8,634,915 B2 | 1/2014 | Mccabe et al. |
| 8,958,876 B2 | 2/2015 | Dong et al. |
| 9,031,651 B2 | 5/2015 | Rockweiler et al. |
| 2005/0145246 A1 | 7/2005 | Hartley et al. |
| 2008/0288023 A1 | 11/2008 | John |
| 2009/0043351 A1 | 2/2009 | Sathaye et al. |
| 2009/0210024 A1 | 8/2009 | M. |
| 2010/0010590 A1 | 1/2010 | Skelton et al. |
| 2010/0262204 A1 | 10/2010 | Mccabe et al. |
| 2010/0305637 A1 | 12/2010 | McCabe et al. |
| 2010/0305638 A1 | 12/2010 | McCabe et al. |
| 2010/0305647 A1 | 12/2010 | Mccabe et al. |
| 2011/0152956 A1 | 6/2011 | Hincapie Ordonez et al. |
| 2012/0035685 A1 | 2/2012 | Saha et al. |
| 2012/0078320 A1 | 3/2012 | Schotzko et al. |
| 2012/0296388 A1 | 11/2012 | Zhang et al. |
| 2013/0060298 A1* | 3/2013 | Splett et al. ................. 607/28 |
| 2013/0261471 A1 | 10/2013 | Saha et al. |
| 2013/0261476 A1* | 10/2013 | Rockweiler et al. ......... 600/510 |
| 2013/0261688 A1 | 10/2013 | Dong et al. |
| 2013/0289640 A1 | 10/2013 | Zhang et al. |
| 2014/0005742 A1 | 1/2014 | Mahajan et al. |
| 2014/0018875 A1 | 1/2014 | Brisben et al. |
| 2014/0088661 A1 | 3/2014 | Hincapie Ordonez et al. |
| 2014/0100626 A1 | 4/2014 | Mccabe et al. |
| 2014/0128933 A1 | 5/2014 | Brooke |
| 2014/0277244 A1 | 9/2014 | Rockweiler et al. |
| 2014/0277280 A1 | 9/2014 | Saha et al. |

OTHER PUBLICATIONS

Mahajan, Deepa, et al., "System and Method for Selection of Pacing Vectors", U.S. Appl. No. 13/925,427, filed Jun. 24, 2013.

Rockweiler, Holly, et al., "Phrenic Nerve Stimulation Detection", U.S. Appl. No. 13/781,177, filed Feb. 28, 2013.

Saha, Sunipa, et al., "Baseline Determination for Phrenic Nerve Stimulation Detection", U.S. Appl. No. 13/781,133, filed Feb. 28, 2013.

* cited by examiner

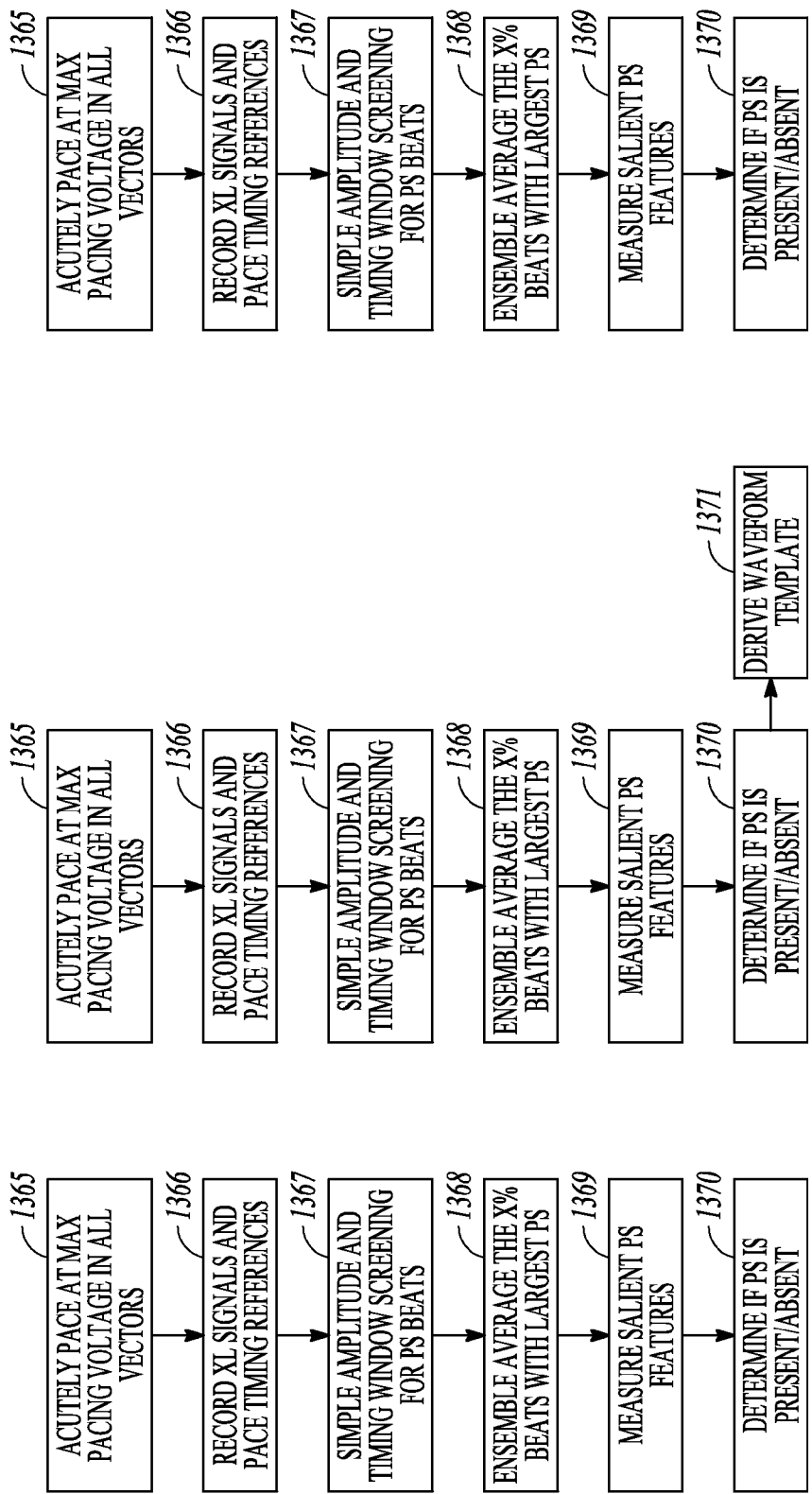

ADAPTIVE PHRENIC NERVE STIMULATION DETECTION

CLAIM OF PRIORITY

This application claims the benefit of priority under 35 U.S.C. §119(e) of U.S. Provisional Patent Application Ser. No. 61/670,870, filed on Jul. 12, 2012, which is herein incorporated by reference in its entirety.

TECHNICAL FIELD

This application is related generally to medical devices and, more particularly, to cardiac stimulation systems, devices and methods that address unintended phrenic nerve stimulation.

BACKGROUND

Implanted cardiac stimulation systems may be used to deliver cardiac resynchronization therapy (CRT) or to otherwise pace the heart. When the heart is paced in the left ventricle (LV), for example, there may be unwanted stimulation of the phrenic nerve that causes contraction of the diaphragm. Unintended phrenic nerve activation (an unintended action potential propagated in the phrenic nerve) is a well-known consequence of left ventricular pacing. The left phrenic nerve, for example, descends on the pericardium to innervate the left part of the diaphragm. In most people, the left phrenic nerve runs close to coronary vein targets for lead implantation. The unintended phrenic nerve activation may cause the diaphragm to undesirably contract. Unintended phrenic nerve activation may feel like hiccups to the patient. Such unintended phrenic nerve activation can occur when the electric field of the LV pacing lead is proximate to the left phrenic nerve and is at a stimulation output that is strong enough to capture the nerve. The unintended phrenic nerve activation may also be referred to herein as pace-induced phrenic nerve stimulation and abbreviated as "PS".

Unintended phrenic nerve activation may vary from patient to patient. One reason for this variance is that the anatomic location of the phrenic nerve can vary within patients. Additionally, the veins are not always in the same location with respect to the ventricle and the nearby passing nerve. Also, the selected vein in which to place a cardiac lead or the location of the pacing electrode for a prescribed cardiac therapy may vary.

Cardiac therapies may be delivered using different pacing configurations and different stimulation parameters. Examples of pacing configurations include LV bipolar, LV to can, and LV to RV (right ventricle) also referred to as "extended bipolar." Examples of stimulation parameters include the amplitude (e.g. voltage) and pulse width. The pacing configuration or the stimulation parameters of a therapy may be modified in an effort to avoid phrenic nerve stimulation. The LV pacing electrodes may be repositioned to capture the LV for a pacing therapy such as CRT while avoiding phrenic nerve capture, or the clinician may decide not to implant an LV pacing electrode but rather rely on other pacing algorithms that do not pace the LV.

Although phrenic nerve stimulation is commonly assessed at implant, unintended phrenic nerve activation caused by phrenic nerve capture during pacing may first appear or worsen post-implant for a variety of reasons such as reverse remodeling of the heart, lead micro-dislodgement, changes in posture, and the like. Therefore, the device may be reprogrammed during special office visits after implant to avoid phrenic nerve stimulation. Electronic repositioning (i.e. changing the pacing configuration) is usually effective, but the vector and stimulation parameter reprogramming can be time consuming. Additionally, PS may be present in all vectors. Knowledge of the PS threshold for each available pacing vector/configuration, along with myocardial capture thresholds, may be used to select a viable or optimal stimulation configuration (e.g. LV pacing configuration) that eliminates or reduces the risk for PS.

It is desirable to provide a more effective way to choose the vector with the biggest safety margin (e.g. largest voltage amplitude different between the thresholds of myocardial stimulation and PS). The amplitude of the PS response is dependent on the pacing output. If an accelerometer is used to sense PS, an amplitude of an accelerometer signal for the PS response can be faint and difficult to detect reliably when the pacing energy level is reduced, especially in the presence of noise. A result may be underestimating the PS onset threshold by estimating the PS onset to be higher than the true onset.

SUMMARY

An example of a system comprises a cardiac pulse generator configured to generate cardiac paces to pace the heart, a sensor configured to sense a physiological signal for use in detecting pace-induced phrenic nerve stimulation (PS), a storage, and a phrenic nerve stimulation detector. The pace-induced phrenic nerve stimulation is phrenic nerve stimulation induced by electrical cardiac pace signals. The storage is configured for use to store patient-specific PS features for PS beats with a desirably large signal-to-noise ratio determined by pacing the heart using a pacing pulse with a large energy output. The PS beats are cardiac paces that induce PS. The phrenic nerve stimulation detector may be configured to detect PS features for the patient by analyzing a PS beat with a desirably large signal-to-noise ratio induced using a pacing pulse with a large energy output (e.g. large voltage, large current, large pulse width or various combinations thereof) and score patient-specific PS features in the storage, and use the patient-specific PS features stored in the storage to detect PS beats when the heart is paced using cardiac pacing pulses with a smaller energy output.

In an example of a method for detecting PS beats in a patient where the PS beats are cardiac paces that induce phrenic nerve stimulation, PS features for the patient are detected. Detecting the PS features may include pacing the heart using a pacing pulse with a large energy output to induce a PS beat with a desirably large signal-to-noise ratio, and analyzing the PS beat with the desirably large signal-to-noise ratio to identify PS features for the patient. The method may include pacing the heart using cardiac pacing pulses with a smaller energy output, and using the PS features to detect PS beats induced by the cardiac pacing pulses with the smaller energy output. In an example the method may include sweeping a pacing energy output according to a protocol, using the PS features to detect PS beats induced by the cardiac pacing pulses, and determining the cardiac pacing pulses with a smallest pacing energy output that induce PS beats.

In an example of a method for selecting a pacing vector from a plurality of available pacing vectors for use to pace a heart of a patient, PS features are detected for PS beats in the patient for each of the plurality of available pacing vectors. The PS beats are cardiac paces that induce phrenic nerve stimulation. Detecting PS features may include, for each of the plurality of available pacing vectors, pacing the heart using a pacing pulse with a large energy output to induce a PS beat with a desirably large signal-to-noise ratio, and analyzing the PS beat with the desirably large signal-to-noise ratio to identify patient-specific PS features. The method may further include pacing the heart for each of the plurality of available pacing vectors using cardiac pacing pulses including sweeping a pacing energy output according to a protocol, using the PS features to detect PS beats induced by the cardiac pacing pulses, and determining a PS threshold for each of the plurality of available pacing vectors, where in the PS threshold is a smallest pacing voltage that induce PS beats. At least one of the plurality of available pacing vectors with a large PS threshold may be identified for use to pace the heart.

This Summary is an overview of some of the teachings of the present application and is not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 13A-C illustrate examples of a method for characterizing PS response.

DETAILED DESCRIPTION

Figure 1:
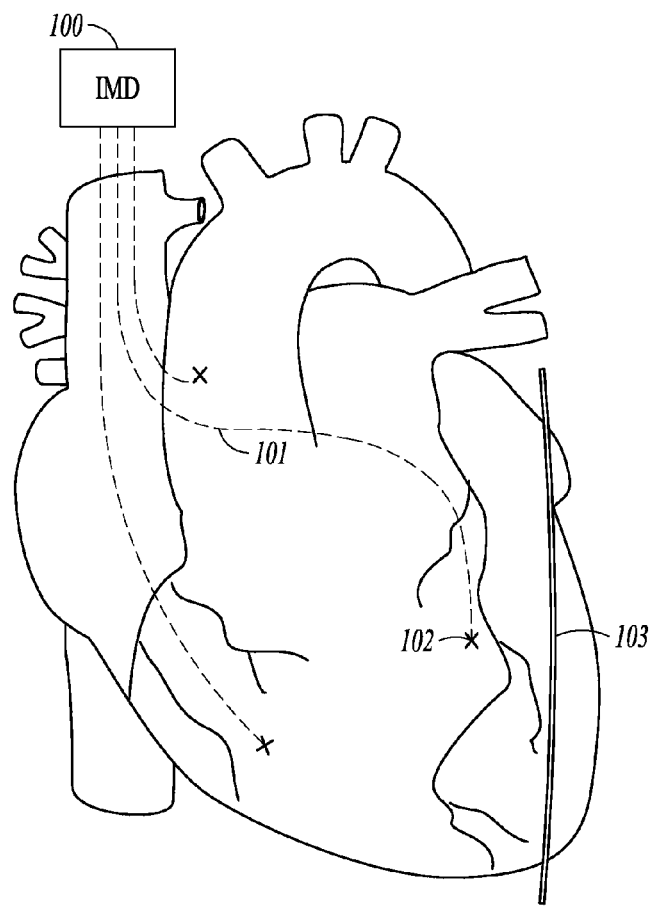
FIG. 1 illustrates, by way of example, an embodiment of an implantable medical device (IMD) configured to deliver myocardial stimulation.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and changes such as structural, logical, and electrical changes may be made without departing from the scope of the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Various embodiments disclosed herein may use high energy output pacing, with a high signal-to-noise ratio, to characterize a PS response for use in detecting PS responses to lower output pacing that have a lower signal-to-noise ratio. The high or large energy output pacing may be characterized by a large voltage, a large current, or a large pulse width in the myocardial stimulation pacing. This document may refer to a large pacing voltage for simplicity and ease of reading. However, it is understood that the large pacing voltage is an example of a large energy output, and that other large energy outputs may include large current, large pulse width, or various combinations of large voltage, current or pulse width. A brief discussion of myocardial stimulation and the phrenic nerve is provided below, followed by discussion of characterizing patient-specific PS responses and using the characterized PS responses to detect PS.

Myocardial Stimulation

A myocardial stimulation therapy may deliver a cardiac therapy using electrical stimulation of the myocardium. Some examples of myocardial stimulation therapies, and devices for performing the therapies, are provided below. A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and then to the ventricular myocardium to provide a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure. Heart failure refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. A CRT example applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-myocardial infarction (MI) and heart failure patients, which appears to reverse remodel the heart as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions may be the trigger for ventricular remodeling. Pacing one or more sites may cause a more coordinated contraction, by providing pre-excitation of myocardial regions which would otherwise be activated later during systole and experience increased wall stress. The pre-excitation of the remodeled region relative to other regions unloads the region from mechanical stress and allows reversal or prevention of remodeling to occur.

Phrenic Nerves

Both a right phrenic nerve and a left phrenic nerve pass near the heart and innervate the diaphragm below the heart. Pace-induced phrenic nerve activation, also referred to herein as PS, may be observed with various forms of pacing. PS may be observed particularly with LV pacing because of the close proximity of the LV pacing site to the left phrenic nerve. PS is a common side effect of CRT. Cardiac stimulation at other locations of the heart may result in PS in either the left or right phrenic nerve. The present subject matter is not limited to PS of the left phrenic nerve during LV pacing, but may be implemented to appropriately address PS in either the left or right phrenic nerve caused by myocardial stimulation.

PS may be observed only when a patient is in a particular position (e.g. lying down) or activity level. The unintended phrenic nerve activation may not have been observed at the time that the stimulation device was implanted because of the patient position at the time of implantation, because of the effects of anesthesia, or because of other factors that are not present in a clinical setting.

Characterizing PS Responses and Detecting PS

Some embodiments, for example, implement a detection algorithm for detecting unintended pace-induced phrenic nerve stimulation ("PS"). According to various embodiments, the PS-detection algorithm can be used in a clinical setting such as during implant procedures or in patient follow-up visits, or an ambulatory setting such as in a patient's home, or in both the clinical and ambulatory setting. The PS-detection algorithm may lessen or alleviate the burden on the patients and clinical staff to adequately address the problems of PS that may occur during myocardial stimulation. For example, the ability to accurately and/or automatically detect PS may reduce prolonged discomfort for patients experiencing PS, and may reduce the burden on hospitals and staff for testing and reprogramming devices.

The PS algorithm is capable of addressing problems with detecting PS. Even when a patient is sitting quietly, it can be difficult to sense signals close to the PS threshold. For example, it can be difficult to process low-peak-to-peak amplitudes of sensed PS responses from the deflection variations observed in the PS sensor (e.g. accelerometer), especially those close to the PS threshold. It can also be difficult to detect PS because different patients have PS responses of various amplitudes. The present subject matter provides a technique to quickly and automatically find the PS threshold in all available pacing vectors. In addition or as an alternative, this technique may be used to find the PS threshold across multiple pacing pulse widths. Weak or low-amplitude PS responses on an accelerometer tracing, for example, can be confused with heart sounds. Characterizing the PS timing and features using high energy paces makes misdetection of heart sounds and PS much less likely.

Accelerometers have been proposed to detect motion caused by PS. Some embodiments may implement algorithms for detecting PS response due to LV pacing using an accelerometer for the implantable pulse generator. For example, the accelerometer used to detect PS responses may be in the implantable pulse generator. However, there are some challenges for detecting PS threshold using accelerometers. Respiration may cause an intermittent signal as the stimulation field is perturbed by respiratory motion. The movement of the heart with each beat/contraction may change the proximity of the pacing electrode to the phrenic nerve. Also, PS amplitudes at the PS onset threshold are often much smaller than at the maximum pacing voltage. The smaller pacing voltages recruit fewer nerve bundles in the phrenic nerve, thus resulting the smaller PS amplitudes. Another challenge is that mechanical wave propagation properties are specific to the patient. Some of these patient-specific mechanical wave propagation properties include variations in amplitude (attenuation), phase, and time delay (wave propagation velocity). This patient-specific wave propagation affects the PS signal detected by the accelerometer. Also, the implantation position and orientation of the pulse generator along with the accelerometer within the pulse generator, may vary with the patient. This also can affect the amplitude, phase and time delay of the PS signal sensed by the accelerometer.

Certain morphological characteristics of evoked PS response signatures are preserved across pacing voltage levels (or other pacing energy outputs) and stimulation configurations/vectors. These characteristics (for example, delay from the LV pace to the first major peak of PS) determined at higher pacing levels can be used to improve detection of faint and/or intermittent PS events more common at lower pacing voltages. Robust detection of lower amplitude PS responses is aided by first characterizing the PS response parameters by using a large pacing voltage (e.g. max voltage LV pacing) to elicit higher amplitude PS. The PS response often becomes stronger and more persistent as the pacing voltage is increased to maximum due to recruitment of more phrenic nerve bundle fibers and associated muscle fibers. These stronger amplitude PS responses are more reliably detected, generally have higher signal-to-noise ratios, and can serve as a "PS template" in adjusting PS-detection algorithm parameters on a patient-specific basis.

The low-amplitude PS responses can be characterized by using high pacing voltages to evoke PS responses with high signal-to-noise (SNR) ratio. These PS responses induced by the high pacing voltages have a higher amplitude, and thus have a higher signal-to-noise (SNR) ratio. The high amplitude PS response is used to measure patient-specific attributes of the PS response. For example, some embodiments may use measured time delays to salient peaks and zero crossings, expected amplitude ranges, and rudimentary spectral characteristics such as peak-to-peak intervals, slew rate, etc. to the patient-specific PS response attributes. These attributes function as a PS template which may be used to detect lower amplitude PS induced by lower pacing voltages. Lower amplitude PS responses have a lower signal-to-noise ratio, which have made it more difficult to determine a PS threshold. Noise sources may include non-diaphragmatic vibrations such as speech, body motion, and may include circuit noise such as thermal noise. Heart sounds which are also pace synchronous and may be temporally close to or overlapping with the PS response may be problematic at low pacing voltages. However, the PS response characteristics are relatively easy to determine at higher pacing thresholds, and it is relatively simple to use these PS response characteristics to characterize the sensed signal at lower pacing voltages, which may be delivered as part of a pacing voltage sweep protocol to detect the PS threshold, to determine if a beat should be characterized as a PS beat. A PS beat can be declared if there is a sufficient match. For example, a PS threshold may be declared for the lowest voltage where M of N (e.g. 3 of 5) PS beat criteria are met.

High pacing voltages may be used to evoke PS responses with high signal-to-noise (SNR) ratio to characterize the PS responses. At high pacing output, the chance of a weak PS response is still possible, but it is less likely to be of clinical consequence because LV pacing output is rarely if ever programmed at max output. Some embodiments may implement a special PS evocation mode for the purpose of characterizing the PS response, where the PS evocation mode temporarily increases the pacing voltage over the maximum programmable pacing voltage/pulse width for the pacing therapy. A separate detection stage tuned to quickly detect PS at high pacing voltages may be used to characterize the PS response.

This algorithm can be used in the context of LV pacing site selection, acute LV vector configuration selection, or an ambulatory system for automatic detection of PS and automatic mitigation via LV vector switching. The algorithm may be used in a CRT pacing system to automatically detect and/or mitigate unwanted extracardiac muscle stimulation or diaphragmatic stimulation.

The present subject is able to provide an adaptive characterization of the PS response that is specific to the patient. A patient-specific set of decision thresholds can be used to account for PS response differences, instead of using a single fixed-parameter set for all of the patients. Further, according to some embodiments, the present subject matter is able to adaptively characterize the PS response for specific stimulation vectors.

FIG. 1 illustrates, by way of example, an embodiment of an implantable medical device (IMD) configured to deliver myocardial stimulation. The illustrated IMD 100 is used to perform a cardiac tissue stimulation therapy, such as CRT or other pacing therapies, using leads represented by the dotted lines and electrodes represented by "X" fed into the right atrium, right ventricle, and coronary sinus of the heart. The lead 101 passing through the coronary sinus of the heart includes a left ventricular electrode 102, or electrodes, for use to stimulate the left ventricle at a stimulation site. FIG. 1 also indicates that the left ventricular electrode 102 of the lead 101 is relatively close to the left phrenic nerve 103. PS may occur for certain stimulation configurations (e.g. pacing vectors, electrode placement, or stimulation parameters).

A PS sensor is a sensor that may be used to detect pace-induced phrenic nerve stimulation (PS). By way of example and not limitation, a PS sensor may include a sensor to detect motion caused by the diaphragm. For example, some embodiments use an accelerometer to detect PS. Other examples of sensors that may be used to detect PS include, but are not limited to, an acoustic sensor, a respiration sensor, an impedance sensor, a neural sensor on the phrenic nerve, or an electromyogram (EMG) sensor for sensing signals indicative of diaphragm contraction.

Figure 2:
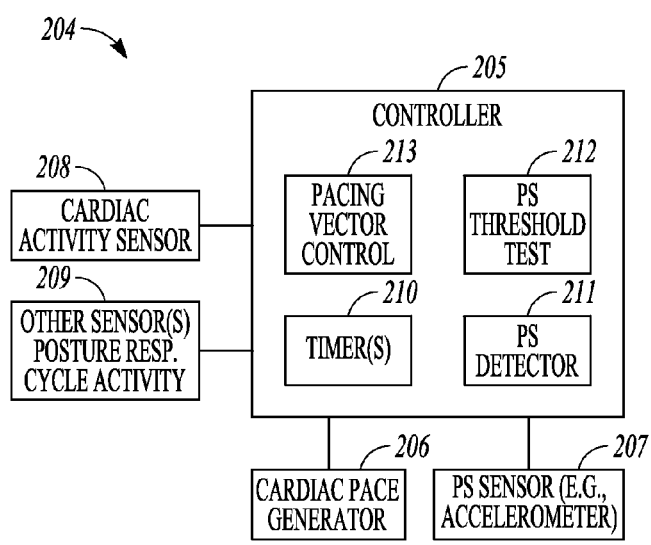
FIG. 2 illustrates, by way of example, an embodiment of an IMD.

FIG. 2 illustrates, by way of example, an embodiment of an IMD. The illustrated IMD 204 may be used to deliver myocardial stimulation, and to detect PS. The illustrated IMD 204 includes a controller 205, a cardiac pace generator 206, and a PS sensor 207. In some embodiments, the IMD 204 may also include a cardiac activity sensor 208 and/or one or more other sensors 209 such as, by way of example and not limitation, a sensor used for detecting posture, a sensor used for detecting respiration or a respiration cycle, or a sensor used for detecting activity. The device may implement a cardiac pacing algorithm, in which the controller 205 receives sensed cardiac activity from the cardiac activity sensor 208, uses timer(s) 210, such as a cardiac pacing timer, to determine a pace time for delivering a cardiac pace or other myocardial stimulation pulse, and controls the cardiac pace generator 206 to deliver the cardiac pace at the desired time. The controller 205 also includes a PS detector 211 that cooperates with the PS sensor 207 to discriminate if a signal from the PS sensor 207 is indicative of PS events. For example, the IMD may include a storage for storing patient-specific PS features for PS beats. As disclosed in this document, the PS beat used to identify the PS features may be induced to provide a desirably large signal-to-noise ratio by pacing the heart using a pacing pulse with a large voltage. The phrenic nerve stimulation detector may be configured to detect PS features for the patient by analyzing a PS beat with a desirably large signal-to-noise ratio induced using a pacing pulse with a large voltage, and use the patient-specific PS features stored in the memory to detect PS beats when the heart is paced using cardiac pacing pulses with a smaller voltage.

In some embodiments, the IMD 204 may be configured with a PS threshold test module 212 used to perform PS threshold test(s). The PS threshold test may use the patient-specific PS features, detected using the large pacing voltage, to determine the lowest or threshold pacing voltage that induces PS. The PS threshold test may be configured to deliver myocardial stimulation using different stimulation parameters. The PS threshold tests may be configured to determine the pacing vectors and/or the myocardial stimulation parameters that cause or that may cause PS ("PS pace or PS beat"), or myocardial stimulation parameters that do not cause PS ("NoPS pace or NoPS beat").

The PS threshold test may be implemented alone as a standalone pacing voltage step-up and/or step-down sequence, or may be implemented in conjunction with a pacing capture threshold test (e.g. LV threshold) such that both the pacing threshold and the PS threshold are determined during the same test procedure. The voltage or pulse width of the pace may be adjusted to provide a desired pace that captures the myocardial tissue without eliciting PS.

The PS threshold test may include pacing the heart using cardiac pacing pulses, including sweeping a pacing voltage according to a fixed or adaptive protocol, using the PS features to detect PS beats induced by the cardiac pacing pulses, and determining the cardiac pacing pulses with a smallest pacing voltage that induce PS beats. Some embodiments of the present subject matter may be configured to detect the presence and threshold of phrenic nerve stimulation (PS) using a step-up test or step-down test or a combination of the step-up and step-down tests. The PS threshold may be determined alone or in conjunction with a pace capture threshold test (e.g. an LV threshold test). An LV threshold test often is a "step-down" test that initially uses a high energy pace to confirm capture of the myocardium and that gradually decrements the pacing energy to determine the lowest pacing energy level that still captures the heart. The PS threshold tests may either adjust the pacing amplitude or pulse width to determine the PS threshold. A pacing output level refers to a pacing energy level that may be based on an amplitude of the paces and/or a pulse width of the paces. In addition, the PS threshold may be determined using a combination of step-up and step-down tests. The step sizes may be predefined, or may be dynamically adjusted based on the observed results during the test.

In a "step-up" test, the pacing voltage may be increased by predefined intervals until PS is observed over several beats or with a high response amplitude. If there is not high confidence that PS has been detected, a PS confirmation step may be conducted. The pacing output may be increased for several cardiac cycles, increasing the likelihood of stimulating the phrenic nerve, to determine if the same PS characteristics are observed. Alternatively or additionally, the pacing output may be decreased to determine the characteristics of NoPS beats for comparison.

In a "step-down" test, the pacing voltage may be decreased by pre-determined intervals until PS is no longer observed over several beats. Alternatively, the pacing output decrease may be adaptively adjusted based on the amplitude of PS response. For instance, a larger pacing output decrease could be employed when a large PS amplitude and high PS frequency are observed.

According to some embodiments, the pacing parameters are adaptively adjusted during a test based on the patient's PS response to quickly and accurately measure PS threshold. For example, some embodiments adjust pacing amplitude output, or pulse width output, or the number of paces at a level, or a combination thereof. Thus, the test can be implemented to determine an appropriate characteristic of a myocardial pace (e.g. an appropriate amplitude and/or pulse width) that avoids PS.

The pacing output for a PS threshold test can be adaptively adjusted based on the PS response. A larger pacing output drop could be used when a higher PS amplitude to baseline ratio or higher frequency is observed. When PS amplitude from multiple steps are observed, a linear or polynomial or other functions may be fitted over the PS response to adjust the pacing output subsequently. A step-up process may be initiated when PS response disappears after the output adjustment.

The physical position of the stimulation electrode or electrodes used to deliver the myocardial stimulation may be adjusted in an attempt to avoid PS, such as may occur during an implantation procedure. A physician may physically move the electrode. Some embodiments may provide electronic repositioning by selecting a set of stimulation electrodes from a larger set of potential stimulation electrodes. In some embodiments, the pacing vector between or among stimulation electrodes may be modified in an attempt to avoid PS. The controller in some IMD embodiments may include a pacing vector control module 213 used to change the pacing vectors. The pacing vectors may be controlled by a clinician through an external programmer, or may be implemented autonomously by the IMD such as may occur in an ambulatory setting.

Figure 3:
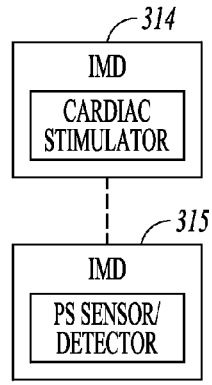
FIG. 3 illustrates, by way of example, an embodiment of a system that includes two or more IMDs.

The PS detection may occur in the same IMD that is providing the myocardial stimulation, or may occur in another IMD. Thus, for example, an accelerometer used to provide the PS detection may be positioned near the diaphragm or near the portion of the diaphragm innervated by the phrenic nerve or near the apex of the heart, which may improve the signal-to-noise characteristics of the sensed signal. FIG. 3 illustrates an embodiment of a system that includes two or more IMDs. A first one of the IMDs 314 in the illustrated system includes a cardiac stimulator configured to deliver myocardial stimulation pulses. By way of example and not limitation, the first IMD may be a pacemaker or other cardiac rhythm management device. A second one of the IMDs 315 in the illustrated system includes a PS detector/sensor used to detect PS that may be caused by the myocardial stimulation pulses delivered from the first one of the IMDs. In some embodiments, the IMDs 314, 315 may communicate with each other over a wired connection. In some embodiments, the IMDs 314, 315 may communicate with each other wirelessly using ultrasound or radiofrequency (RF) or other wireless technology.

Some embodiments may use an IMD with a pacing lead, and an accelerometer on the pacing lead to provide the PS detection. Thus, for example, an accelerometer on the lead may be positioned near the diaphragm or near the portion of the diaphragm innervated by the phrenic nerve or near the apex of the heart, which may improve the signal-to-noise characteristics of the sensed signal.

The sensor(s) used for detecting PS may be implanted or may be external. The algorithms for processing the sensed signals to detect PS may be performed within the IMD(s) and/or may be performed in external devices. By way of example, some embodiments may use implantable sensor(s) and use external device(s) to process the sensed signals to detect PS. The monitoring of the patient for PS may be performed in a clinical setting or in an ambulatory setting. This monitoring, regardless of whether it is performed in the clinical setting or an ambulatory setting, may be performed using implanted PS detectors such as illustrated in FIGS. 2-3, for example, and/or may be performed using external PS detectors.

Figure 4:
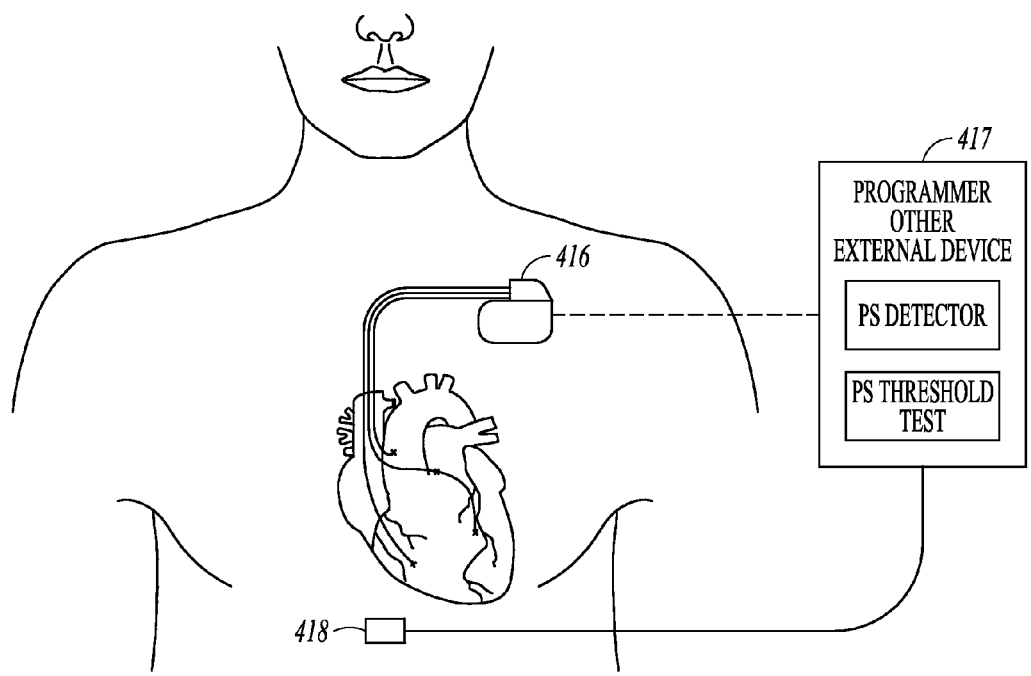
FIG. 4 illustrates, by way of example, an embodiment of a system that includes an IMD, an external device, and an external phrenic nerve stimulation (PS) sensor.

FIG. 4 illustrates an embodiment of a system that includes an IMD 416, such as a cardiac rhythm management device, an external device 417 such as a programmer, and an external PS sensor 418. The system may be implemented in a clinical setting, such as by a clinician who uses a programmer to program the IMD, or may be implemented in an ambulatory setting to occasionally check if the myocardial stimulation is causing PS. In various embodiments, the external device includes a PS detector that cooperates with the PS sensor to discriminate if a signal from the PS sensor indicates the presence of PS events. In various embodiments, the external device includes a PS threshold test module used to perform PS threshold test(s). The PS threshold test may be configured to control the IMD to deliver myocardial stimulation using different stimulation parameters. The PS threshold tests may be configured to determine the myocardial stimulation parameters that cause or that may cause PS, or myocardial stimulation parameters that do not cause PS. The physical position of the stimulation electrode or electrodes used to deliver the myocardial stimulation may be adjusted in an attempt to avoid PS, such as may occur during an implantation procedure. In some embodiments, the pacing vector between or among stimulation electrodes may be modified in an attempt to avoid PS. In some embodiments, the external PS sensor 418 may be integrated with the external device 417, such that the PS may be sensed by holding or otherwise positioning the external device next to the patient (e.g. externally positioned near the diaphragm or near the apex of the heart).

Figure 5:
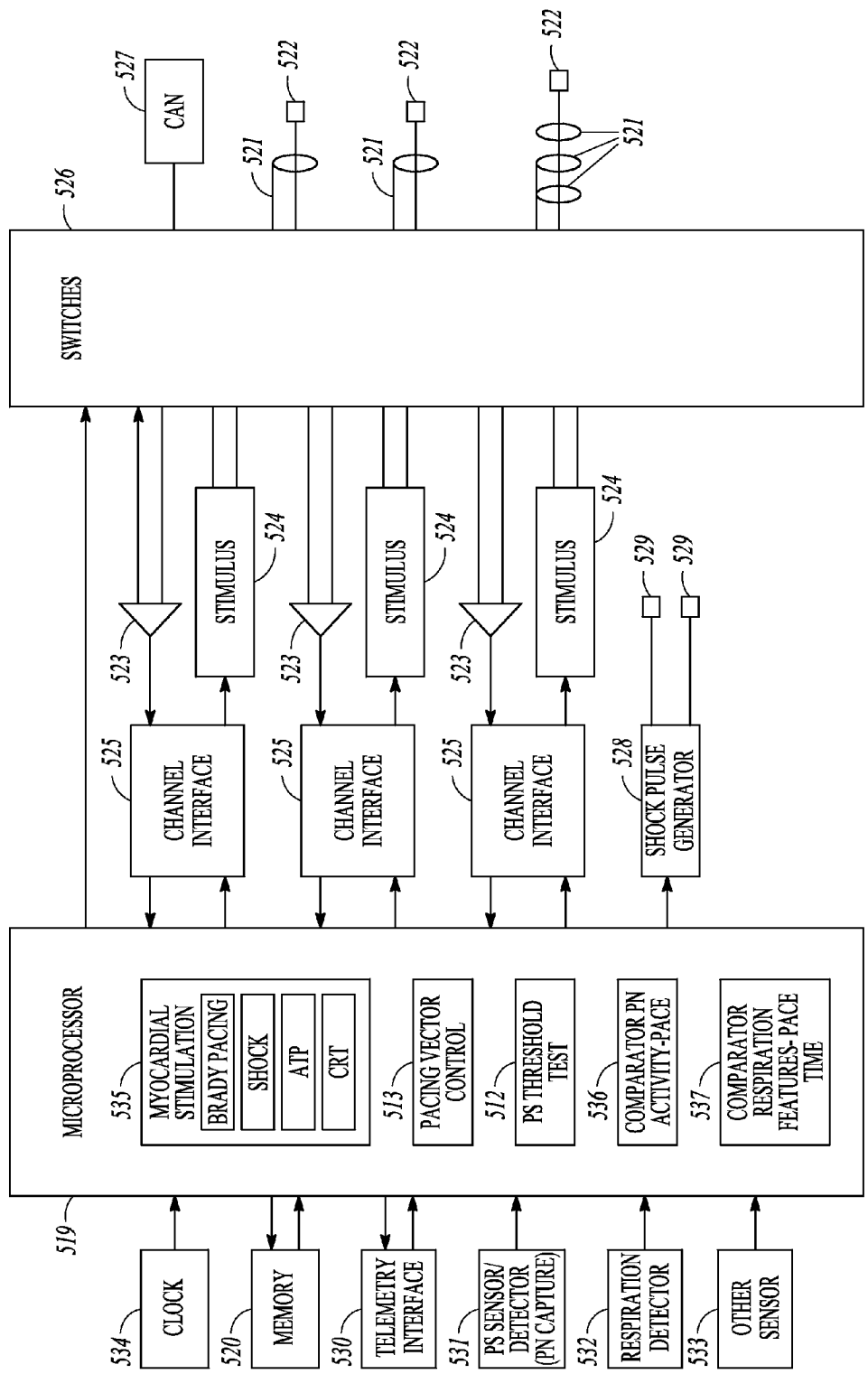
FIG. 5 illustrates, by way of example, a system diagram of an embodiment of a microprocessor-based implantable device.

FIG. 5 illustrates a system diagram of an embodiment of a microprocessor-based implantable device. The controller of the device is a microprocessor 519 which communicates with a memory 520 via a bidirectional data bus. The controller could be implemented by other types of logic circuitry (e.g., discrete components or programmable logic arrays) using a state machine type of design. The "logic circuitry" may include discrete logic circuitry, firmware, microprocessor programming, or various combinations thereof. The system illustrated in the figure has, by way of example, three sensing and pacing channels comprising leads with ring electrodes 521 and tip electrodes 522, sensing amplifiers 523, pulse generators 524, and channel interfaces 525. One of the illustrated leads includes multiple ring electrodes 521, such as may be used in a multi-polar lead. An example of a multipolar lead is a left ventricle quadripolar lead. In some embodiments, the leads of the cardiac stimulation electrodes are replaced by wireless links. Each channel thus includes a pacing channel made up of the pulse generator connected to the electrode and a sensing channel made up of the sense amplifier connected to the electrode. The channel interfaces communicate bidirectionally with the microprocessor, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects intrinsic chamber activity, termed either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each lead are connected via conductors within the lead to a switching network 526 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in unipolar or an extended bipolar mode using only one of the electrodes of the lead with the device housing (can) 527 or an electrode on another lead serving as a ground electrode. In some embodiments, a shock pulse generator 528 may be interfaced to the controller, in addition or alternative to other stimulation channels, for delivering a defibrillation shock via a pair of shock electrodes 529 to the atria or ventricles upon detection of a shockable tachyarrhythmia. A can electrode may be used to deliver shocks. The figure illustrates a telemetry interface 530 connected to the microprocessor, which can be used to communicate with an external device. As illustrated in FIG. 5, the system may include a PS sensor/detector 531 used to detect unintended phrenic nerve activations caused by myocardial stimulation. Various embodiments may also include a respiration detector 532 and/or other sensor(s) 533 such as may be used to provide contextual information like activity and posture. According to various embodiments, the phrenic nerve activity detector may include, but is not limited to, an accelerometer, an acoustic sensor, a respiration sensor, impedance sensors, neural sensor on the phrenic nerve, or electrodes to sense electromyogram signals indicative of diaphragm contraction. Various embodiments use more than one detector or sensor to provide a composite signal that indicates phrenic nerve capture. The use of more than one detector or sensor may enhance the confidence in detecting PS events. The illustrated embodiment also includes a clock 534 that may be used to control timing within the device.

According to various embodiments, the illustrated microprocessor 519 may be configured to perform various cardiac tissue (e.g. myocardial) stimulation routines 535. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT). As illustrated, the controller 519 may also include a comparator 536 to compare time when phrenic nerve activity is detected to a pace time to determine that phrenic nerve activity is attributed to the pace, and/or may include a comparator 537 to compare respiration features to the pace time for use in detecting PS. The illustrated microprocessor 519 may include instructions for performing a PS threshold test 512 and a pacing vector control process 513, similar to the controller 205 illustrated in FIG. 2

Figure 6:
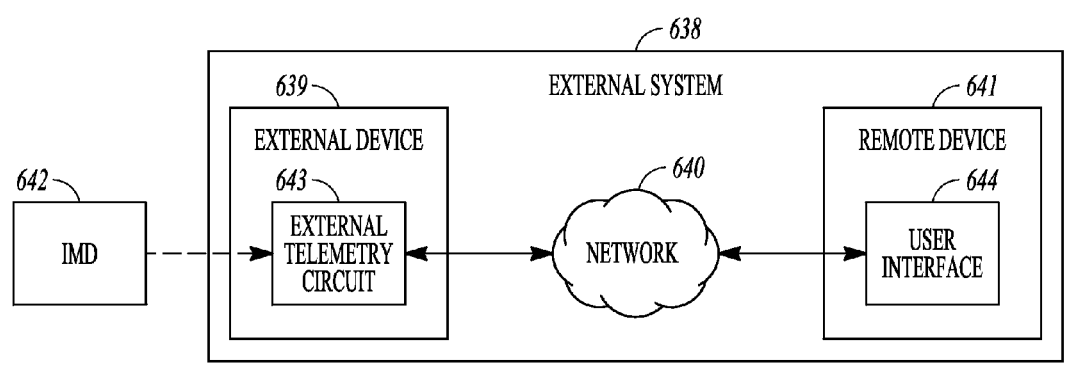
FIG. 6 is a block diagram illustrating, by way of example, an embodiment of an external system.

FIG. 6 is a block diagram illustrating an embodiment of an external system 638. For example, the system may be used to remotely program the implanted device in an ambulatory patient, or to remotely obtain detected PS events from an ambulatory patient, or to remotely retrieve sensed data from the implanted device in an ambulatory patient for analysis of the sensed data for the PS event in a remote location from the ambulatory patient. The external system may include a programmer, in some embodiments. In the illustrated embodiment, the external system includes a patient management system. As illustrated, the patient management system may include an external device 639, a telecommunication network 640, and a remote device 641 removed from the external device 639. The external device 639 is placed within the vicinity of an IMD 642 and includes an external telemetry system 643 to communicate with the IMD 642. The remote device(s) is in one or more remote locations and communicates with the external device through the network, thus allowing a physician or other caregiver to monitor and treat a patient from a distant location and/or allowing access to various treatment resources from the one or more remote locations. The illustrated remote device includes a user interface 644. According to various embodiments, the external device includes a programmer or other device such as a computer, a personal data assistant or phone. The external device, in various embodiments, includes two devices adapted to communicate with each other over an appropriate communication channel, such as a computer by way of example and not limitation. The external device can be used by the patient or physician to provide feedback indicative of patient discomfort, for example.

The present subject matter may be used to detect PS characteristics for each available pacing vector, which may be used to determine a PS threshold for each vector and a desirable stimulation vector. This may be particularly desirable for multi-polar leads. For example, a system may include a plurality of pacing electrodes. The system may be configured to select pacing electrodes from the plurality of pacing electrodes to provide a pacing vector, and control a selection of pacing vectors from a plurality of available pacing vectors for use to pace the heart. The system may detect PS features for PS beats in the patient for each of the plurality of available pacing vectors, by pacing the heart using a pacing pulse with a large voltage to induce a PS beat with a desirably large signal-to-noise ratio, and analyzing the PS beat with the desirably large signal-to-noise ratio to identify patient-specific PS features. The system may pace the heart for each of the plurality of available pacing vectors using cardiac pacing pulses by sweeping a pacing voltage according to a fixed or adaptive protocol, using the PS features to detect PS beats induced by the cardiac pacing pulses, and determining a PS threshold for each of the plurality of available pacing vectors. The system may be configured to identify at least one of the plurality of available pacing vectors that has a large PS threshold for use to pace the heart. For example, the pacing vector with a large PS threshold may be considered to provide a desirably large safety margin for pacing the heart while avoiding PS.

Figure 7:
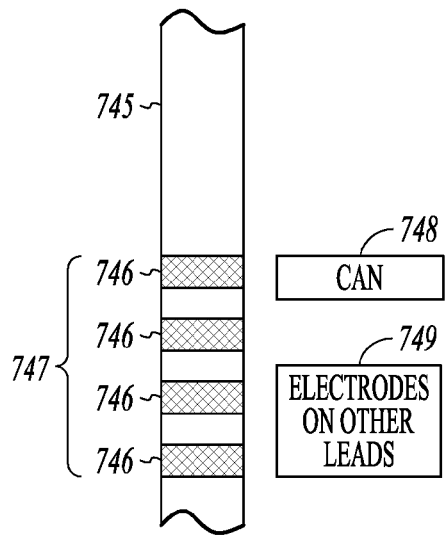
FIGS. 7-9B illustrate, by way of example, some multipolar leads.
Figure 8:
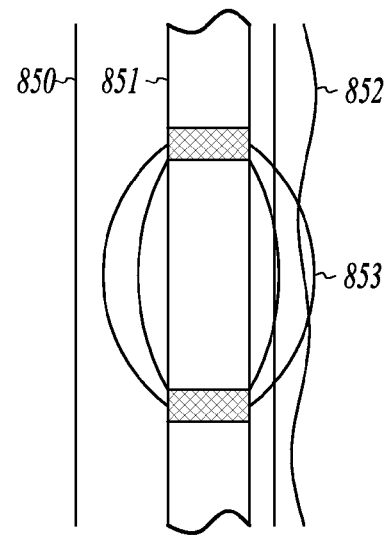
Figure 9A:
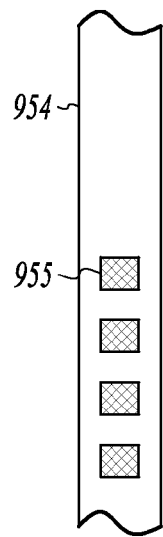
Figure 9B:
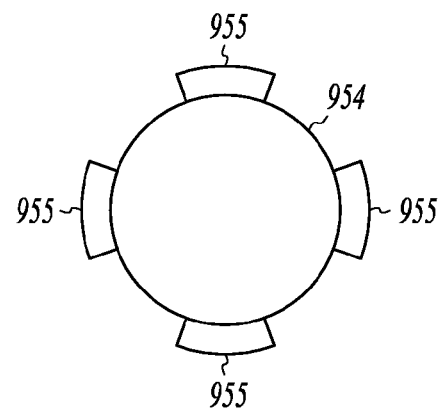

FIG. 7 illustrates an embodiment of a multi-polar lead 745 with annular stimulation electrodes 746 that form an electrode region 747, according to various embodiments. Any one or combination of the annular stimulation electrodes on the lead can be used to provide a stimulation vector to deliver the neural stimulation. Other potential stimulation vectors may be formed using can electrode(s) 748 on the housing of the implanted pulse generator, or from electrode(s) on other lead(s) 749. FIG. 8 illustrates lead electrodes within a lumen, according to various embodiments. The figure illustrates a lumen 850 (e.g. a tributary of the coronary sinus), a lead 851 within the lumen, and a phrenic nerve 852 external to the lumen. The myocardial stimulation generates an electrical field 853 between the electrodes that may extend past the lumen wall to the phrenic nerve 852. This electric field, delivered to stimulate myocardial tissue, may also cause PS. FIGS. 9A and 9B illustrate an embodiment of a lead 954 with stimulation electrodes 955, where the illustrated electrodes do not circumscribe the lead.

These figures illustrate, by way of example and not limitation, some examples of multi-polar leads. A subset of the electrodes can be selected to provide directional stimulation. A test routine can cycle through the available electrodes for use in delivering the stimulation to determine which electrodes are most desirable to provide effective myocardial stimulation while avoiding PS. The test routine may employ a pacing voltage sweep protocol to determine the PS threshold, which is the lowest amplitude cardiac pace that also induces PS.

Figure 10:
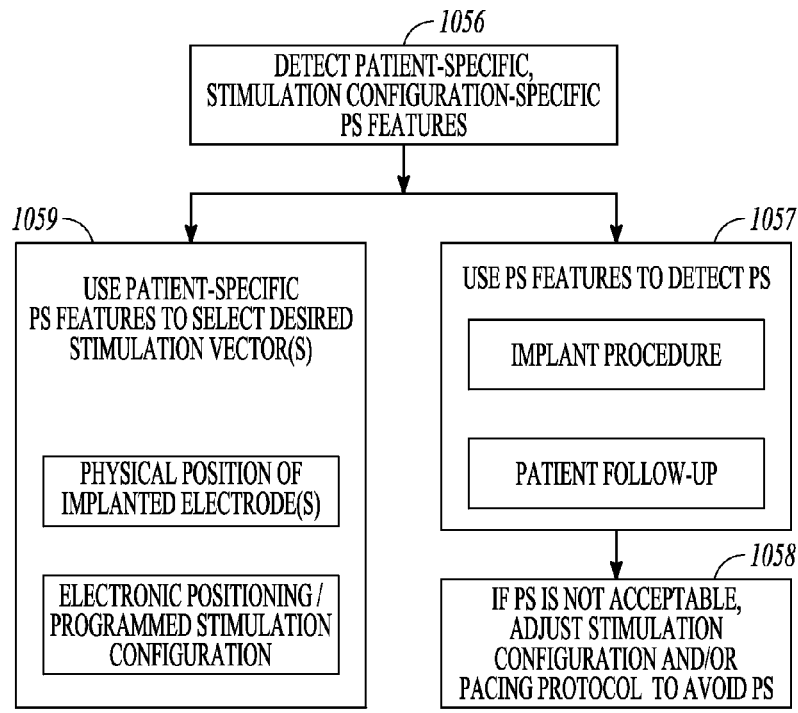
FIG. 10 illustrates an example of a method for characterizing PS, and using the characterized PS.

FIG. 10 illustrates an example of a method for characterizing PS, and using the characterized PS. At 1056, PS features can be detected that are both specific to the patient and to the stimulation configuration. A high energy output pace is delivered for a given pacing vector for the patient, and the resulting PS response, if any, is characterized to provide PS features. These PS features may be used, as generally illustrated at 1057, to detect PS during the implant procedure or at patient follow-up. As generally illustrated at 1058, the stimulation configuration and/or pacing protocol may be adjusted to avoid the detected PS. These PS features may be used, as generally illustrated at 1059, to select a desired stimulation vector or vectors. For example, the position of the electrodes may be physically moved during the implantation procedure, or the programmed stimulation configuration of the electrodes may be changed ("electronic repositioning") to provide effective myocardial stimulation with the highest PS threshold or the largest margin between myocardial and PS capture.

Figure 11:
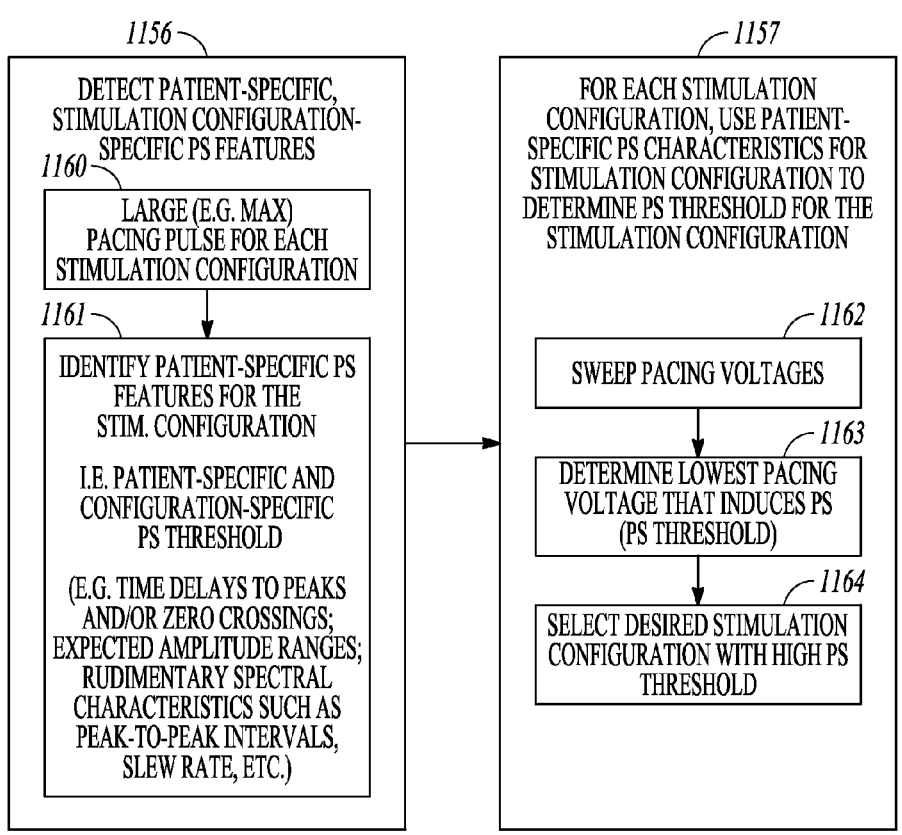
FIG. 11 illustrates an example of a method for detecting PS features and using the detected PS features to detect a PS threshold.

FIG. 11 illustrates an example of a method, illustrated generally at 1156, for detecting PS features, such as was illustrated at 1056 in FIG. 10, and using the detected PS features to detect a PS threshold 1157. At 1160, a large pacing pulse is delivered for each stimulation configuration. For example, a "max" pacing voltage may be used. The max pacing voltage may be the largest pacing voltage that the device is programmed to deliver under normal operating conditions. The max pacing voltage may be a programmable ceiling set by a clinician, or may be a limit set by the device manufacturers. Some embodiments may implement a special PS evocation mode for the purpose of characterizing the PS response, where the PS evocation mode temporarily increases the pacing voltage over the maximum programmable pacing voltage/pulse width for the pacing therapy. The PS threshold may be determined for each stimulation configuration where PS is observed, as generally illustrated at 1157. For example, a protocol for sweeping pacing voltages (e.g. high to low voltages or low to high voltages) may be implemented 1162. The PS threshold for the pacing vector is determined by determining the lowest pacing voltage that induced PS 1163. The desired stimulation configuration may be selected as a configuration that provides a high PS threshold 1164.

Figure 12:
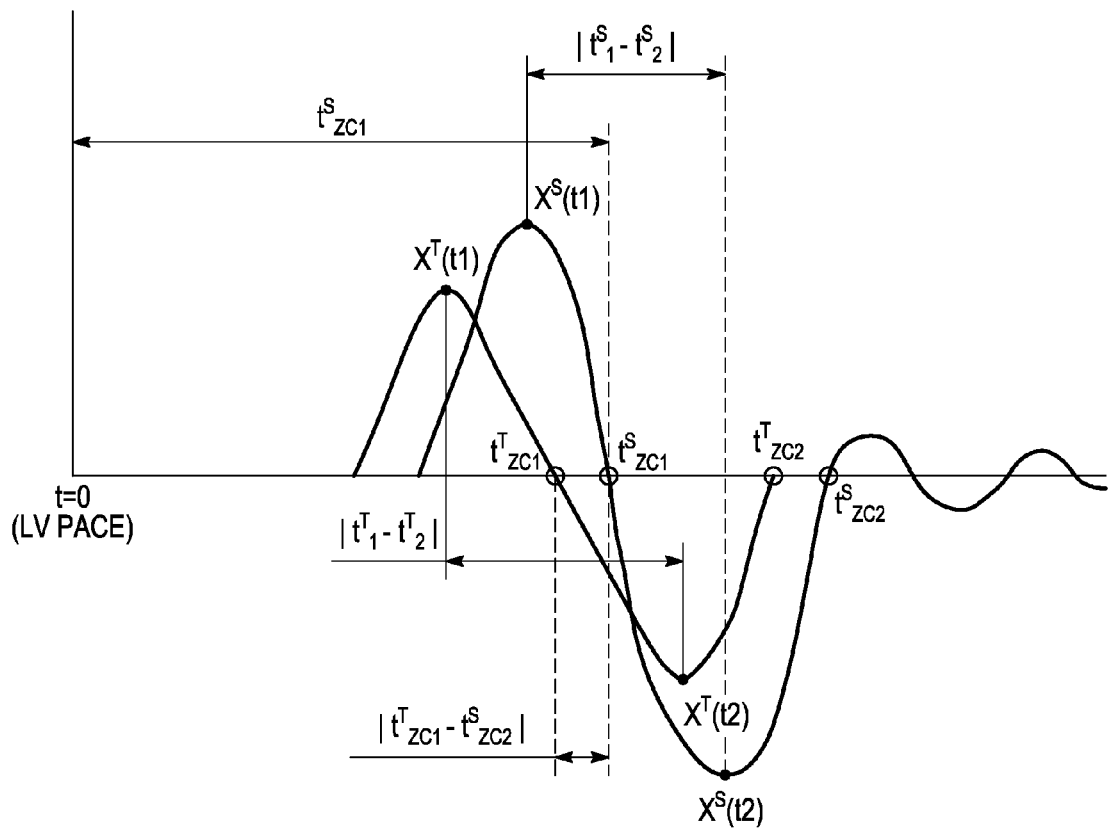
FIG. 12 illustrates, by way of example and not limitation, some potential PS response characteristics for a PS template signal.

Various embodiments may detect PS characteristics using a large pacing voltage (e.g. a maximum pacing voltage or otherwise large pacing voltage with desirable signal-to-noise characteristics). These characteristics may be used to discriminate if PS occurred during the cardiac cycle, such as may be performed by a PS detector. The nominal values for a PS response to the maximum pacing stimulation may be referred to as a template. By way of example, the PS response to the maximum pacing stimulation may be evaluated by identifying peak characteristics and zero crossing characteristics of the PS signal to provide the template signal. The superscript T used below represents template values. For example, nominal values for a PS response may include: a time ($t^T_1$) to a first peak and an amplitude of the accelerometer $X^T$ at this first time $X^T(t^T_1)$; a time ($t^T_2$) to a second peak and an amplitude of the accelerometer at this second time $X^T(t^T_2)$; a zero crossing time ($t^T_{ZC1}$) to a zero crossing between first and second peaks; and a zero crossing time ($t^T_{ZC2}$) to a zero crossing after the second peak. These are illustrated in the template waveform provided in FIG. 12. Also illustrated in FIG. 12 is a sensed signal ($X^S$) to be analyzed using the nominal values of the template signal (T). A PS beat may be declared if the comparison of the nominal values for the sensed signal favorably correspond to the measured feature values for the template. For example, a PS beat may be declared if:

$(|t^T_{ZC1} - t^S_{ZC1}| < 11$ msec$)$; AND $(t^S_{ZC1} < 60$ msec$)$; AND $|t^S_1 - t^S_1| < 40$ msec; AND $1 - (|t^T_1 - t^T_2|/|t^S_1 - t^S_2|) < 0.35$; AND $|X^S(t^S_1) - X^S(t^S_2)| > 1.5 * m_{BG}$ where $m_{BG}$ is the estimate of the mean peak-to-peak amplitude of the background noise of the signal; AND $|X^S(t^S_1) - X^S(t^S_2)| > \text{MAX}(10 \text{ mG}, 0.5 * |X^T(t^T_1) - X^T(t^T_2)|)$; AND $|X^S(t^S_1) - X^S(t^S_2)| > \text{MAX}(10 \text{ mG}, 0.25 * |X^T(t^T_1) - X^T(t^T_2)|)$ AND $$\text{Sign}(X^T(t^T_1)) = \text{Sign}(X^S(t^S_1)) \text{ AND } \text{Sign}(X^T(t^T_2)) = \text{Sign}(X^S(t^S_2))$$

This is provided as an example. Other signal features, constants, and threshold values may be used. Also, various embodiments may use any one or any combination of two or more of these features. Further, the values (e.g. msec, Hz, %, mG) used to characterize these features may be changed without departing from the scope of the present subject matter.

Some embodiments may use M of N logic (e.g. 3 of 5) on detections to declare PS onset threshold voltage FIGS. 13A-C illustrate examples of a method for characterizing PS response. As generally illustrated in FIG. 13A, a procedure is implemented to acutely pace at a large or max pacing voltage in all vectors 1365. This large pacing voltage results in a relatively large PS response if any PS response occurs. For example, a max pacing voltage for a given vector results in the largest PS response possible for that vector. The accelerometer signal and pace timing references are recorded at 1366. A simple amplitude and timing window may be used to screen for PS beats 1367. Beats with the largest PS response may be ensemble averaged at 1368. Ensemble averaging may include generating a normalized sum of accelerometer waveforms aligned by the LV pace time reference. The ensemble average will lessen or minimize the effect of outliers and will reduce noise on the XL signal. The salient features of the PS response may be measured 1369, which may be used to determine if PS is present or absent 1370. Other embodiments are illustrated, by way of example, in FIGS. 13B-C. FIG. 13B, for example, is similar to the method illustrated in FIG. 13A, but also derives a waveform template 1371 that is characterized using the PS features. FIG. 13C, for example, is similar to the method illustrated in FIG. 13A, but also derives a waveform template 1371 from the average from the largest X % of beats.

Figure 14A:
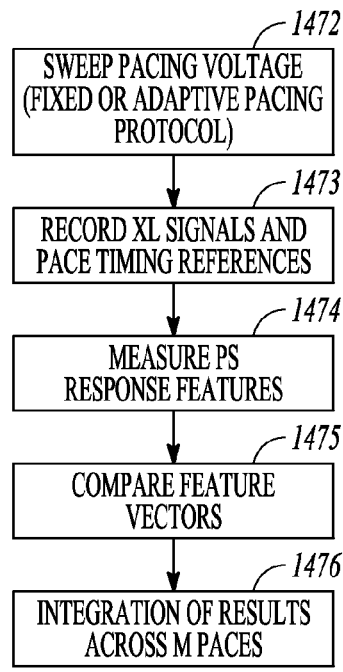
FIGS. 14A-D illustrate examples of a method for detecting PS beats using the characterized PS response.
Figure 14B:
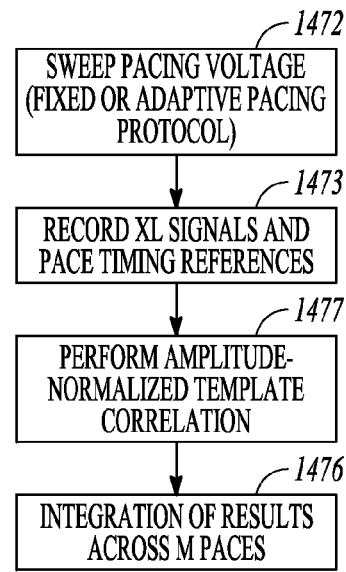
Figure 14C:
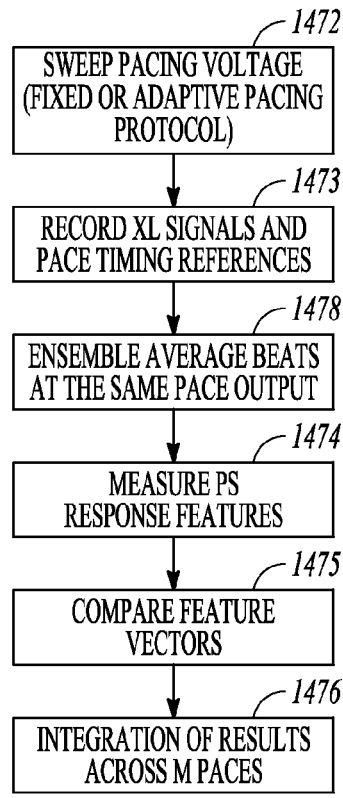
Figure 14D:
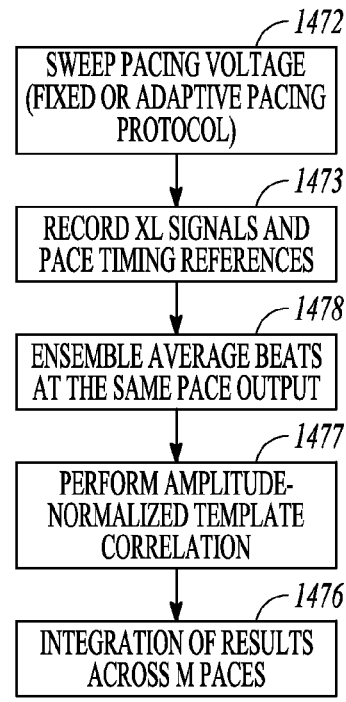

FIGS. 14A-D illustrate examples of a method for detecting PS beats using the characterized PS response. As generally illustrated in FIG. 14A, a fixed or adaptive pacing voltage sweep is implemented at 1472. The accelerometer signal and pace timing references are recorded at 1473, and the PS response features of the accelerometer signal are measured at 1474. At 1475, the feature vectors for the sensed signal may be compared to the feature vectors of characterized PS response (e.g. "PS template"). Feature vectors are known in the art of pattern recognition. A feature vector represents an object using an n-dimensional vector of numerical features. The analysis may be performed for a number of paces ("M paces"), and the results may be integrated over these M paces as illustrated at 1476. Other embodiments are illustrated, by way of example, in FIGS. 14B-D. FIG. 14B, for example, illustrates that an amplitude-normalized template correlation 1477 may be performed rather than measuring PS response features 1474 and comparing feature vectors 1475 which were illustrated in FIG. 14A. FIG. 14C, for example, illustrates that a number of beats for a given pace level may be ensembled and averaged together 1478 before measuring the PS response features. FIG. 14D is similar to FIG. 14B, for example, illustrating that a number of beats for a given pace level may be ensembled and averaged together 1478 before performing the amplitude-normalized template correlation.

Figure 15:
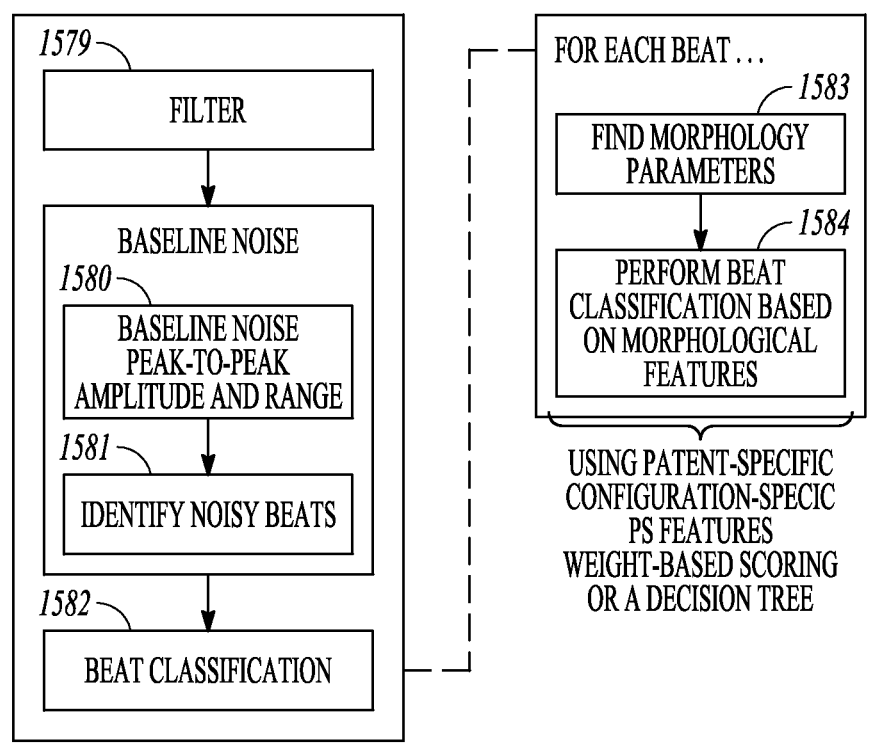
FIG. 15 illustrates, by way of example, an embodiment of a procedure for using a PS template and morphological features of a sensor-based signal to discriminate between cardiac paces that induce phrenic nerve stimulation and cardiac paces that do not induce phrenic nerve stimulation).

FIG. 15 illustrates, by way of example, an embodiment of a procedure for using a PS template and morphological features of a sensor-based signal to discriminate between PS beats (cardiac paces that induce phrenic nerve stimulation) and NoPS beats (cardiac paces that do not induce phrenic nerve stimulation). As provided herein, the determination of a valid PS template is based a simplified set of criteria (e.g. peak amplitudes and timings relative to pace, spectral characteristics, etc.) In the illustrated embodiment, for example, a sensed signal may be filtered 1579. Signals are appropriately prefiltered to remove low frequency respiration components or movements and high frequency noise.

Baseline signal levels 1580 may be used to identify and remove noisy beats 1581 from the discrimination procedure. Various embodiments may estimate a baseline level of a sensor-based signal, which may be used in the PS detection may be used to perform signal-to-noise ratio calculations and to discriminate between NoPS (paced heart beats without PS) and PS beats (paced heart beats with PS) (see U.S. Provisional Application 61/616,296 entitled "Baseline Determination for Phrenic Nerve Stimulation Detection," filed on Mar. 27, 2012 and incorporated herein by reference in its entirety). Some embodiments of the present subject matter may be configured to dynamically determine a baseline level of sensor-based signals used to detect PS. Detection of PS uses the PS characteristics identified using the large pacing voltage that increases the signal-to-noise ratio of the PS beats. Since the PS response characteristics are adaptively adjusted for each patient, it is possible to detect PS beats with lower signal-to-noise ratios. The baseline level determination may provide further improvements for detecting PS in the signal from the PS sensor. The dynamic determination of the baseline level improves the device's ability to automatically differentiate PS events from other events in the sensor signal by accommodating context-specific differences in the sensed signal.

The remaining beat signals can be classified as PS beats or NoPS beats at 1582 using the PS template. For example, as illustrated at 1583 the beat signal is analyzed to identify morphological parameters that can be used to characterize specific features of the beat signal, which can then be used to classify the beat signal as a PS beat or NoPS beat, at 1584. PS may not occur for a given pacing vector/pacing configuration. Thus, even at high pacing levels, various processes may be performed to determine if a PS beat has occurred before the characteristics of the PS beat can be extracted to provide a PS template. Further, when detecting the PS threshold using the PS template, various processes may be performed to analyze the sensed signal against the PS template. Various embodiments may use PS-detection techniques, including clustering and correlation techniques to detect PS, feature-based techniques for detecting PS, and combinations thereof (see U.S. Provisional Application 61/616,300 entitled "Determination of Phrenic Nerve Stimulation Threshold," filed on Mar. 27, 2012 and incorporated herein by reference in its entirety; and U.S. Provisional Application 61/616,305 entitled "Phrenic Nerve Stimulation Detection," filed on Mar. 27, 2012 and incorporated herein by reference in its entirety). PS detectors use sensor-based signals to determine when PS occurs. An example of a sensor-based signal is an accelerometer signal. However, the correlation process for detecting PS may be implemented with other PS detectors that are not accelerometer-based. For example, PS sensor signals such as impedance, muscle activity, respiration, nerve activity, and the like may be analyzed, in a certain window around the pace, and correlated with the PS template to determine if the paced beat is a PS beat or a NoPS beat. The sensing window can be defined relative to a pace time. For example, if concerned about LV pacing causing PS, the sensing window can be defined relative to an LV pace time or relative to an RV pace time plus an LV offset. By way of examples, and not limitation, the window may be defined to be about 20 ms to 100 ms, or may be defined to be about 40 ms to 70 ms after the LV pace. Other ranges may be used. Such windows help avoid heart sounds or other noise in the sensed signals. According to various embodiments, all data points, or certain data points, or select features of the PS sensor signal within the sensing window may be correlated to the template signal. A "match" can be declared, indicating a PS beat, if the signal or a portion of the signal within the sensing window exceeds a certain degree of correlation (e.g. >0.9) with the PS template.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a sequence of instructions which, when executed by one or more processors, cause the processor(s) to perform the respective method. In various embodiments, the methods are implemented as a set of instructions contained on a computer-accessible medium such as a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
   a cardiac pulse generator configured to generate cardiac pacing pulses to pace the heart, wherein the cardiac pulse generator is configured to generate cardiac pacing pulses throughout a range of cardiac pacing energy outputs, wherein:
      cardiac pacing energy outputs above a myocardial capture threshold capture myocardia for a cardiac tissue stimulation therapy, and
      cardiac pacing energy outputs above a pace-induced phrenic nerve stimulation (PS) threshold, which is larger than the myocardial capture threshold, induce PS which is undesirable for the cardiac tissue stimulation therapy;
   a sensor configured to sense a physiological signal for use in detecting PS, wherein an amplitude of the physiological signal is dependent on the cardiac pacing energy output such that increasing cardiac pacing energy output increases the amplitude and decreasing cardiac pacing energy output decreases the amplitude;
   a storage for storing a patient-specific PS template of patient-specific PS features for use to detect PS beats, wherein the PS beats are cardiac paces that induce PS; and
   a phrenic nerve stimulation detector configured to create the patient-specific PS template and use the template to detect PS beats, including:
      control the cardiac pulse generator to intentionally deliver a PS beat, including generate cardiac pacing pulses with a large cardiac pacing energy output that is significantly larger than the PS threshold, detect the patient-specific PS features for the patient by analyzing the physiologic signal that results from the intentionally-delivered PS beat, and store the patient-specific PS features for the template in the storage;
      control the cardiac pulse generator to decrease the pacing energy output from the large energy output to a smaller cardiac pacing energy output; and
      use the patient-specific PS features for the template in the storage to analyze the physiologic signal for detecting PS beats when the heart is paced using cardiac pacing pulses with the smaller cardiac pacing energy output.

2. The system of claim 1, wherein the system is configured to perform a PS threshold test that includes:
   pacing the heart using cardiac pacing pulses, including sweeping a pacing energy output according to a protocol; and
   using the patient-specific PS template of patient-specific PS features to detect PS beats induced by the cardiac pacing pulses; and
   determining the cardiac pacing pulses with a smallest pacing energy output that induce PS beats.

3. The system of claim 2, wherein the protocol includes a fixed or adaptive pacing protocol.

4. The system of claim 2, further comprising a plurality of pacing electrodes, wherein the system is configured to:
   select pacing electrodes from the plurality of pacing electrodes to provide a pacing vector;
   control a selection of pacing vectors from a plurality of available pacing vectors for use to pace the heart;
   create a patient-specific template of PS features for PS beats in the patient for each of the plurality of available pacing vectors for each of the plurality of available pacing vectors, by pacing the heart using a pacing pulse with a large energy output significantly larger than the PS threshold, and analyzing the physiologic signal that results from the large energy output to identify patient-specific PS features;
   pace the heart for each of the plurality of available pacing vectors using cardiac pacing pulses by sweeping a pacing energy output according to a protocol, using the PS features to detect PS beats induced by the cardiac pacing pulses, and determining a PS threshold for each of the plurality of available pacing vectors, where in the PS threshold is a smallest pacing energy output that induce PS beats.

5. The system of claim 4, wherein the system is configured to identify at least one of the plurality of available pacing vectors that has a large PS threshold for use to pace the heart.

6. The system of claim 1, wherein the phrenic nerve stimulation detector is configured to use the patient-specific PS features stored in the memory to detect PS beats.

7. The system of claim 1, wherein to detect the patient-specific PS features, the phrenic nerve stimulation detector is configured to screen for PS beats in a timing window and ensemble an average of the largest detected PS beats.

8. The system of claim 1, wherein the patient-specific PS features include peak characteristics and zero crossing characteristics of at least one sensed PS beat signal, wherein to use the patient-specific PS features for the template in the storage to detect PS beats, the phrenic nerve stimulation detector is configured to compare a sensed signal to the peak characteristics and the zero crossing characteristics of the at least one sensed PS beat signal.

9. The system of claim 8, wherein the patient-specific PS features include:
   a time from a pace to and an amplitude of a first peak;
   a time from the pace to and an amplitude of a second peak;
   a time from the pace to a zero crossing between first and second peaks; and a time from the pace to a zero crossing after the second peak.

10. The system of claim 8, wherein to compare the sensed signal to the peak characteristics and the zero crossing characteristics of the at least one sensed PS beat signal, the phrenic nerve stimulation detector is configured to compare feature vectors between the measured features in the sensed signal and the patient-specific PS features.

11. The system of claim 8, wherein to compare the sensed signal to the peak characteristics and the zero crossing characteristics of the at least one sensed PS beat signal, the phrenic nerve stimulation detector is configured to perform an amplitude-normalized correlation between measured features in the sensed signal and the patient-specific PS features.

12. A method for detecting PS beats in a patient, wherein the PS beats are cardiac paces that induce phrenic nerve stimulation (PS), the method comprising:
   creating a patient-specific PS template of PS features, including:
      pacing the heart using a pacing pulse with a large cardiac pacing energy output that is significantly greater than a PS threshold to intentionally deliver a PS beat, wherein cardiac pacing energy outputs above the PS threshold induce PS; and
      sensing and analyzing a physiological signal that results from the intentionally-delivered PS beat to identify the PS features for the patient-specific template, wherein an amplitude of the physiological signal is dependent on the cardiac pacing energy output such that increasing cardiac pacing energy output increases the amplitude and decreasing cardiac pacing energy output decreases the amplitude;
   pacing the heart using cardiac pacing pulses with a smaller energy output; and
   using the PS features for the patient-specific template to detect PS beats when the heart is paced with the smaller energy output.

13. The method of claim 12, wherein the PS features include peak characteristics and zero crossing characteristics of at least one sensed PS beat signal.

14. The method of claim 13, wherein the PS features include:
   a time from a pace to and an amplitude of a first peak;
   a time from the pace to and an amplitude of a second peak;
   a time from the pace to a zero crossing between first and second peaks; and
   a time from the pace to a zero crossing after the second peak.

15. The method of claim 12, wherein using the PS features for the patient-specific template to detect PS beats includes comparing feature vectors between measured features in a sensed signal and the PS features.

16. The method of claim 12, wherein using the PS features for the patient-specific template to detect PS beats includes performing an amplitude-normalized correlation between measured features in a sensed signal and the PS features.

17. The method of claim 12, wherein creating the patient-specific template includes screening for PS beats in a timing window and ensembling an average of the largest detected PS beats.

18. The method of claim 12, further comprising detecting a PS threshold for PS beats including:
   sweeping a pacing energy output according to a protocol to pace the heart using the cardiac pacing pulses; and
   determining the cardiac pacing pulses with a smallest pacing energy output that induce PS.

19. The method of claim 18, wherein:
   the PS features include peak characteristics and zero crossing characteristics of at least one sensed PS beat signal; and
   using the PS features for the patient-specific template to detect PS beats includes:
      comparing feature vectors between measured features in a sensed signal and the PS features; or
      performing an amplitude-normalized correlation between measured features in a sensed signal and the PS features.

20. A method for selecting a pacing vector from a plurality of available pacing vectors for use to pace a heart of a patient, comprising:
   creating a patient-specific PS template of PS features for PS beats for each of the plurality of available pacing vectors, wherein the PS beats are cardiac paces that induce phrenic nerve stimulation, and creating the patient-specific template includes, for each of the plurality of available pacing vectors, pacing the heart using a pacing pulse with a large cardiac pacing energy output that is significantly greater than a PS threshold to intentionally deliver a PS beat, wherein cardiac pacing energy outputs above the PS threshold induce PS, and sensing and analyzing a physiological signal that results from the intentionally-delivered PS beat to identify the PS features for the patient-specific template;
   pacing the heart for each of the plurality of available pacing vectors using cardiac pacing pulses including sweeping a cardiac pacing energy output according to a protocol, using the PS features for the patient-specific template to detect PS beats when the heart is paced with a smaller cardiac energy output than the large cardiac pacing output, and determining the PS threshold for each of the plurality of available pacing vectors; and
   identifying at least one of the plurality of available pacing vectors with a large PS threshold for use to pace the heart.

* * * * *